United States Patent [19]
Cook et al.

[11] Patent Number: 5,635,488
[45] Date of Patent: Jun. 3, 1997

[54] COMPOUNDS HAVING PHOSPHORODITHIOATE LINKAGES OF HIGH CHIRAL PURITY

[75] Inventors: Phillip D. Cook, San Marcos, Calif.; Glenn Hoke, Mt. Airy, Md.

[73] Assignee: Isis Pharmaceuticals, Inc., Carlsbad, Calif.

[21] Appl. No.: 470,129

[22] Filed: Jun. 6, 1995

Related U.S. Application Data

[63] Continuation-in-part of Ser. No. 297,703, Aug. 29, 1994, Pat. No. 5,506,212, and Ser. No. 58,023, May 5, 1993, Pat. No. 5,521,302, which is a division of Ser. No. 777,670, Oct. 15, 1991, Pat. No. 5,212,295, which is a continuation-in-part of Ser. No. 777,007, Oct. 16, 1991, abandoned, said Ser. No. 297,703, is a continuation of Ser. No. 777,007.

[51] Int. Cl.$^6$ .......................... A61K 31/70; C07H 21/00
[52] U.S. Cl. ................. 514/44; 514/42; 514/43; 536/25.33; 536/25.34
[58] Field of Search ....................... 536/23.1, 25.33, 536/25.34; 514/44

[56] References Cited

U.S. PATENT DOCUMENTS

| | | | |
|---|---|---|---|
| 3,336,289 | 8/1967 | Wechter et al. | 536/27 |
| 3,687,808 | 8/1972 | Merrigan et al. | 536/27 |
| 3,792,039 | 2/1974 | Erickson et al. | 536/28 |
| 3,846,402 | 11/1974 | Eckstein et al. | 536/27 |
| 4,310,662 | 1/1982 | Crea | 537/27 |
| 4,500,707 | 2/1985 | Caruthers et al. | 536/27 |
| 4,591,614 | 5/1986 | Miller et al. | 525/54.11 |
| 4,663,446 | 5/1987 | Wright | 536/28 |
| 5,138,045 | 8/1992 | Cook et al. | 536/27 |
| 5,166,195 | 11/1992 | Ecker | 514/44 |
| 5,212,295 | 5/1993 | Cook | 536/26.7 |
| 5,248,670 | 9/1993 | Draper et al. | 514/44 |
| 5,506,212 | 4/1996 | Hoke et al. | 514/44 |
| 5,521,302 | 5/1996 | Cook | 536/25.31 |

FOREIGN PATENT DOCUMENTS

| | | |
|---|---|---|
| 0506242 | 9/1992 | European Pat. Off. |
| 45-11506 | 4/1970 | Japan |
| 48-07354 | 3/1973 | Japan |
| WO89/03683 | 5/1989 | WIPO |
| WO91/08313 | 6/1991 | WIPO |

OTHER PUBLICATIONS

Bryant, F. and Benkovic, S., "Stereochemical course of the reaction catalyzed by 5'-nucleotide phosphodiesterase from snake venom", *Biochemistry* 1979, 2825–2628.

Burgers, P. and Eckstein, F., "A study of the mechanism of DNA polymerase I from *Escherichia coli* with diastereomeric phosphorothioate analogs of deoxyadenosine triphosphate", *J. of Biological Chemistry* 1979, 254(15), 6889–6893.

Burgers, P. and Eckstein, F., "Absolute configuration of the diastereomers of adenosine 5'-O-(1-thiotriphosphate): Consequences for the stereochemistry of polymerization by DNA-dependent RNA polymerase from *Escherichia coli*", *Proc. Natl. Acad. Sci. USA* 1978, 75(10), 4798–4800.

Brody, R. and Frey, P., "Unambiguous determination of the stereochemistry of nucleotidyl transfer catalyzed by DNA polymerase I from *Escherichia coli*", *Biochemistry* 1981, 20, 1245–1252.

Brody, R. et al., "Stereochemical coruse of nucleotidyl catalyzed by bacteriophage T7 induced DNA polymerase", *Biochemistry* 1982, 21, 2570–2572.

Cruse et al., "Chiral Phosphorothioate Analogues of B–DNA", *J. Mol. Biol.* 1986, 192, 891–905.

Daluge et al., "Synthesis and Antimicrobial Activity of a Carbocyclic Puromycin Analog-6-Dimethylamino-9-{R-[2r-hydroxy-3R-(p-methoxyphenyl-L-alanylamino)]-cyclopentyl}purine", *J. of Medicinal Chem.* 1971, 14, 820–823.

Eckstein, F and Jovin, T.M., "Assignment of Resonances in the Phosphorus–31 Nuclear Magnetic Resonance Spectrum of Poly[d(A–T)] from Phosphorothioate Substitution", *Biochemistry* 1983, 2, 4546–4550.

Eckstein, F., "Nucleoside Phosphorothioates", *J. Am. Chem. Soc.* 1966, 88, 4292.

Eckstein, F., "Nucleoside Phosphorothioates", *J. Am. Chem. Soc.* 1970, 92, 4718–4723.

Doerr and Fox, "Nucleosides. XL. The Introduction of a 2,3'-Imino Bridge into Pyrimidine Nucleosides", *J. Am. Chem.* 1967, 89, 1760–1761.

Haga, K. et al., "The preparation of halo–nucleosides", *Bull. of the Chem. Soc. Jpn.* 1970, 43, 3922–3924.

Fuji, et al., "Acylphosphonates. 7.$^1$ A New Method for Stereospecific and Stereoselective Generation of Dideoxyribonucleoside Phosphorothioates via the Acylphosphonate Intermediates", *Tetrahedron* 1987, 43, 3395–3407.

Gupta, et al., "Template–Primer–Dependent Turnover of (Sp)–dATP S by T4 DNA Polymerase", *J. Bio. Chem.* 1982, 247, 7689–7692.

Goodchild, "Conjugates of Oligonucleotides and Modified Oligonucleotides: A Review of Their Synthesis and Properties", *Bioconjugate Chem.* 1990, 1, 165–187.

Koole, L.H. et al., "Enhanced stability of a Watson & Crick DNA duplex structure by methylation jof the phosphate groups in one strand", *Proc. K. Ned. Acad. Wet.* 1987, 90(1), 41–46.

Jäger, A. et al., "Oligonucleotide N-alkylphosphoramidates: Synthesis and binding to polynucleotides", *Biochemistry* 1988, 27, 7237–7246.

(List continued on next page.)

*Primary Examiner*—James O. Wilson
*Attorney, Agent, or Firm*—Woodcock, Washburn, Kurtz, Mackiewicz & Norris

[57] ABSTRACT

Sequence-specific phosphorothioate oligonucleotides comprising nucleoside units which are joined together by either substantially all Sp or substantially all Rp phosphorothioate intersugar linkages are provided. Such sequence-specific phosphorothioate oligonucleotides having substantially chirally pure intersugar linkages are prepared by enzymatic or chemical synthesis. Sequence-specific phosphorodithioate oligonucleotides are also provided. Such sequence-specific phosphorodithioate oligonucleotides are prepared by chemical synthesis. They are especially well suited as diagnostics, therapeutics and research reagents.

8 Claims, No Drawings

OTHER PUBLICATIONS

Holy, A. and Sorm, F., "Oligonucleotidic compounds. XXXII. Phosphorylation of 1-lyxofuranosyl, 1-xylofuranosyl and 1-arabinofuranosyl derivatives of uracil and thymine with triethyl phosphite and hexachloroacetone", *Collection Czechoslov. Chem. Commun.* 1969, 34, 1929–1953.

Holy, A., "Nucleic acid components and their analogues. IC. synthesis of 6-azauridine 5'-methanephosphonate and 6-azauridine 2'(3')-methanephosphonate", *Collection Czechoslov. Chem. Commun.* 1967, 32, 3713–3718.

Lee, W.W. et al., "Xylo- and Arabinofuranosylthioguanine and Related Nucleosides Derived from 2-Acetamido-6-chloropurine", *J. of Medicinal Chem.* 1971, 14, 820–823.

Ikehara et al., "Purine Cyclonucleosides-8 Selective Sulfonylation of 8-Bromoadenosine Derivatives and an Alternate Synthesis of 8,2'-and 8,3'-S-Cyclonucleosides", *Tetrahedron* 1970, 26, 4251–4259.

Kondo, K. et al., "Studies on biologically active nucleosides and nucleotides.3. synthesis of 9-(3-bromo-3-deoxy-2,5-di-O-acetyl-B-D-xylofuranosyl) adenine", *J. Org. Chem.* 1977, 42(24), 3957–3958.

Goodman, L. and Hubert-Habart, M., "The Direct Formation of a 3',5'-Cyclic Mononucleotide from an Adenine Nucleoside", *Chem. Commun.* 1969, 740–741.

Letters, R. et al., "$O^2$,3'-Cyclouridine", *J. Chem. Soc.* 1961, 1410–1413.

Lichtenthaler, F.W. et al., *Chem. Ber.* 1969, 102, 964.

Niewiarowski, W., et al., "Diastereomers of Thymidine 3'O-(Methanephospono-thioate): Synthesis, Absolute Configuration and Reaction with 3'-methoxyacetylthymidine Under Conditions of Triester Approach to Oligonucleotide Synthesis", *Acta Biochimica Polonia* 1987, 34, 217–231.

Stec, "Oligonucleotides as Antisense Inhibitors of Gene Expression: Therapeutic Implications", *Meeting Abstracts, Abstracts of Papers: Polish Academy of Science*, Jun. 18–21, 1989.

Scheit, Karl Heinz, "Nucleotides with Modified Phosphate Groups", in Nucleotide Analogs John Wiley & Sons, 1980, Chapter Four and Chapter Six.

Suzaki et al., "Synthesis of 9-β-D-Xylofuranosyl-6-mercaptopurine and 9-β-D-Xylofuranosylguanine 5'-Phosphate", *Chem. Pharm. Bull.* 1970, 18, 172–176.

Marumoto, R. et al., "One-Step Halogenation at the 2'-Position of Uridine, and Related Reactions of Cytidine and $N^4$-Acetylcytidine", *Chem.Pharm.Bull.* 1974, 22, 128–134.

Mizuno, Y. et al., "Synthesis of Potential Antimetabolites. XV. Syntheses of a Sulfonate Analog of Adenosine 5'-Phosphate and an Alternative Synthesis of 5',8-S-Anhydroadenine Nucleosides and 5'-Deoxyspongoadenosine and Its Isomers", *J.Org.Chem.* 1974, 39, 1440–1444.

Reese, "The Chemical Synthesis of Oligo- and Polynucleotides by the Phosphotriester Approach", *Tetrahedron* 1978, 34, 3143–3179.

Robins et al., "Nucleic acid related compounds. 11. adenosine 2',3'-ribo-epoxide. synthesis, intramolecular degradation, and transformation into 3'-sustituted xylofuranosyl nucleosides and the lyxo-epoxide[1,2]", *J. Org. Chem.* 1974, 39(11), 1564–1570.

Miller, P.S. et al., "Biochemical and Biological Effects of Nonionic Nucleic Acid Methylphosphonates", *Biochemistry* 1981, 20, 1874–1880.

Stec et al., "Reversed-phase High-performance Liquid Chromatographic Separation of Diastereomeric Phosphorothioate Analogues of Oligodeoxyribonucleotides and Other Backbone-Modified Congeners of DNA", *J. Chromatography* 1985, 326, 263–280.

Romaniuk, P. J. and Eckstein, F., "A study of the mechanism of t4 DNA polymerase with diastereomeric phosphorothioate analogues of deoxyadenosine triphosphate", *Biological Chemistry* 1982, 257(13), 7684–7688.

Ueda, T. et al., "Phosphorothioate-containing RNAs show mRNA activity in the prokaryotic translation systems in vitro", *Nucleic Acids Research* 1991, 19, 547–552.

Uhlmann, E. and Peyman, A., "Antisense oligonucleotides: A new therapeutic principle", *Chemical Reviews* 1990, 90(4), 578–584.

Murray, A.W. et al., "Adenosine 5'-Phosphorothioate. A Nucleotide Analog That Is a Substrate, Competitive Inhibitor, or Regulator of Some Enzymes That Interact with Adenosine 5'-Phosphate", *Biochemistry* 1968, 4023–4029.

Mizuno, Y. et al., "A Novel Synthesis of Purine β-D-Nucleosides via Purine 8,5'-S-Anhydronucleosides", *J.Am.Chem.Soc.* 1972, 94, 4737–4739.

Miller, N. et al., "Nucleosides. XXI. Synthesis of Some 3'-Substituted 2',3'-Dideoxyribonucleosides of Thymine and 5-Methylcytosine", *J. Org. Chem.* 1964, 29, 1772–1776.

Szarek et al., "Synthesis of 5-Deoxy-D-xylo-Hexose and 5-Deoxy-L-arabino-Hexose, and Their Conversion into Adenine Nucleosides", *Carbohydrate Res.* 1978, 62, 89–103.

Schuman, D. et al., *J. Am. Chem. Soc.* 1970, 92, 3434.

Reist et al., "Synthesis of 9-(5-Deoxy-B-D-arabinofuranosyl) adenine", *J. Org. Chem.* 1965, 30, 3401–3403.

Wiberg, "Physical Organic Chemistry", John Wiley & Sons, New York, 1964, p. 424.

Letsinger et al., "Effects of pendant groups at phosphorus on binding properties of d-ApA analogues", *Nucleic Acids Res.* 1986, 14, 3487–3499.

Wempen, I. and Fox, "Nucleosides. LV. Synthesis of a sulfur-bridged thymine anhydro nucleoside and derivatives", *J. Org. Chem.* 1969, 34, 1020–1025.

Wijnen, M.H., "Disproportionation and Recombination Reactions of Methyl and n-Pentyl Radicals", *J. Am. Chem. Soc.* 1961, 83, 3752–3754.

Cohen, J., "Oligonucleotides Inhibitors of Gene Expression", CRC Press, Boca Raton, FL, 1989, pp. 7–116, 137–210.

Guga, P. and Okruszek, A., "Stereospecific conversion of p-chiral nucleoside phosphorothioates", *Tetrahedron Letters* 1984, 25, 2897–2900.

Jarvest, R.L. and Lowe, G., "Synthesis of methyl (R)-and (S)-[$^{18}$O]phosphorothioates and determination of the absolute configuration at phosphorus of the diasteroisomers of adenosine 5'-(1-thiotriphosphate)", *J.C.S. Chem. Comm.* 1979, 364–366.

Lee, Choongeun and Suhadolnik, Robert J., "2',5'-Oligoadenylates Chiral at Phosphorus: Enzymatic Synthesis, Properties, and Biological Activities of 2',5'-Phosphorothioate Trimer and Tetramer Analogues Synthesized from (Sp)-ATPαS", *Biochemistry* 1985, 24(3), 551–555.

Lesnikowski et al., "Octa(thymidine methanephosphonates) of partially defined stereochemistry: synthesis and effect of chirality at phosphorous on binding to pentadecadeoxyriboadenylic acid", *Nucleic Acids Res.* 1990, 18(8), 2109–2115.

Richard, J. P. and Frey, P. A., "Stereochemical coourse of phosphoanhydride synthesis", *Journal of the American Chemical Society* 1983, 105, 6605–6609.

Sammons, R. Douglas and Frey, Perry A., "Synthesis of $R_p$ and $S_p$ [α–$^{18}$O]ADP from $S_p$ and $R_p$ β–Cyanoethyl–Adenosine 5'-[1-Thiodiphosphate]", *J. Biol. Chem.* 1982, 257(3), 1138–1141.

Sopchik et al., "$^{17}$O NMR of Diastereomeric 3',5'-Cyclic Thymidine Methyl Phosphates, Methylphosphonates, and N,N–Dimethyl Phosphoramidates. Phosphorus Configuration of P–Chiral [$^{17}$O, $^{18}$O]–Nucleoside Phosphate Diesters", *Tetrahedron Letters* 1989, 30(10), 1221–1224.

Stec et al., "Synthesis and Absolute Configuration of P–Chiral O–Isopropyl Oligonucleotide Triesters", *Tetrahedron Letters* 1985, 26(18), 2191–2194.

Stec et al., "Solid–Phase Synthesis, Separation, and Stereochemical Aspects of P–Chiral Methane– and 4,4'–Dimethoxytriphenylmethanephosphonate Analogues of Oligodeoxyribonucleotides", *J. Org. Chem.* 1985, 50(20), 3908–3913.

Van Pelt, Jean E. et al., "Gentamicin Nucleotidyltransferase: Stereochemical Inversion at Phosphorus in Enzymatic 2'–Deoxyadenyl Transfer to Tobramycin", *J. Biol. Chem.* 1986, 261(34), 15995–15999.

Tsai, M. D., "Stereochemistry of the hydrolysis of adenosine 5'–thiophosphate catalyzed by venom 5'–nucleotidase", *Biochemistry* 1980, 19, 5310–5316.

Ludwig, J. and Eckstein, F., "Rapid and efficient synthesis of nucleoside 5'–O–(1–thiotriphosphates), 5'–triphosphates and 2',3'–cyclophosphorothioates using 2–chloro–4H–1,3, 2–benzodioxaphosphorin–4–one", *J. Org. Chem.* 1989, 54, 631–635.

Henthorn, P., "Expression of a human placental alkaline phosphatase gene in transfected cells: use as a reporter for studies of gene expression", *Proc. Natl. Acad. Sci. USA* 1988, 85, 6342–6346.

Minshull and Hunt, "The Use of Single–stranded DNA and RNase H to Promote Quantitative Hybrid Arrest of Translation of mRNA/DNA Hybrids in Reticulocyte Lysate Cell--free Translation", *Nucleic Acids Res.* 1986, 14, 6433–6451.

Rothenberg et al., "Oligodeoxynucleotides as anti–sense inhibitors of gene expression: therapeutic implication", *National Cancer Institute* 1989, 81(20), 1539–1565.

Agrawal, S., et al., "Oligodeoxynucleoside Phosphoramidites and Phosphorothioates as Inhibitors of Human Immunodeficiency Virus", *PNAS USA* 1988, 85, 7079–7083.

Dagle et al., "Pathways of Degradation and Mechanism of Action of Antisense Oligonucleotides in *Xenopus laevis* Embryos", *Antisense Res. and Dev.* 1991, 1, 11–20.

Dagle et al., "Physical properties of oligonucleotides containing phosphoramidate–modified internucleoside linkages", *Nucleic Acids Res.* 1991, 19, 1805–1810.

Dagle et al., "Targeted degradation of mRNA in *Xenopus* oocytes and embryos directed by modified oligonucleotides: studies of An2 and cyclin in embryogenesis", *Nucleic Acids Res.* 1990, 18, 4751–4757.

Eder, P.S. and Walder, J.A., "Ribonuclease H from K562 Human Erythroleukemia Cells", *The J. of Biol. Chem* 1991, 266(10), 6472–6479.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucleic Acids Research*, 1987, 15, 5749–5763.

Stec, W. and Lesnikowski, "Stereospecific Synthesis of P–Chiral Analogs of Oligonucleotides", in Methods in Molecular Biology, Agrawal, S., ed., vol. 20, 1992, pp. 285–313.

Stec, W. et al., "Novel Route to Oligo(Deoxyribonucleoside Phosphorothioates). Stereocontrolled Synthesis of P–chiral Oligo(Deoxyribonucleoside Phosphorothioates)", *Nucleic Acids Res.* 1991, 19, 5883–5888.

Zimm, S. et al., "Cerebrospinal Fluid Pharmacokinetics of Intraventricular and Intravenous Aziridinylbenzoquinone", *Cancer Research* 1984, 44, 1698–1701.

Ettinger, L. et al., "Intrathecal Methotrexate Overdose Without Neurotoxicity", *Cancer* 1978, 41, 1270–1273.

Luer, M. and Hatton, "Vancomycin Administration into the Cerebrospinal Fluid: A Review", *The Annals of Pharmacotherapy* 1993, 27, 912–921.

Follmann, H. et al., "Interaction of Ribonucleotide Reductase with Ribonucleotide Analogs", *Biochemistry* 1971, 10, 186–187.

Seela, F. et al., "Phosphoramidites of (oxygen–18) Chiral (Rp)—and (Sp) –configurated Dimer–blocks and Their Use in Automated Oligonucleotide Synthesis", *Nucleosides and Nucleotides* 1987, 6(1–2), 451–456.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTGGGGTT        8

( 2 ) INFORMATION FOR SEQ ID NO: 2:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGACTATGCA AGTAC        15

( 2 ) INFORMATION FOR SEQ ID NO: 3:

( i ) SEQUENCE CHARACTERISTICS:
        ( A ) LENGTH: 55 bases
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTACTTGCAT AGTCGATCGG AAAATAGGGT TCTCATCTCC CGGGATTTGG        50

TTGAG        55

( 2 ) INFORMATION FOR SEQ ID NO: 4:

( i ) SEQUENCE CHARACTERISTICS:
        ( A ) LENGTH: 41 bases
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTCAACCAAA TCCCGGGAGA TGAGAACCCT ATTTTCCGAT C        41

( 2 ) INFORMATION FOR SEQ ID NO: 5:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GACTATGCAA GTAC               14

COMPOUNDS HAVING PHOSPHORODITHIOATE LINKAGES OF HIGH CHIRAL PURITY

CROSS REFERENCE TO RELATED APPLICATIONS

This application is a continuation-in-part of U.S. patent application Ser. No. 08/297,703, filed Aug. 29, 1994, now U.S. Pat. No. 5,506,212 which is a continuation of U.S. patent application Ser. No. 07/777,007, filed Oct. 16, 1991, now abandoned. This application also is a continuation-in-part of U.S. patent application Ser. No. 08/058,023, filed May 5, 1993, now U.S. Pat. No. 5,521,302 which is a divisional application of U.S. patent application Ser. No. 07/777,670, filed Oct. 15, 1991 (issued as U.S. Pat. No. 5,212,295, issue date May 18, 1993), which is a continuation-in-part of U.S. patent application Ser. No. 07/777,007 filed Oct. 16, 1991, now abandoned. Each of the above-mentioned applications is commonly assigned with this application, and the entire disclosures of each are herein incorporated by reference.

FIELD OF THE INVENTION

This invention is directed to sequence-specific phosphorothioate and phosphorodithioate oligonucleotides comprising nucleosides joined by intersugar linkages, and to their synthesis and use. More particularly, the phosphorothioate intersugar linkages linking the nucleosides of oligonucleotides of the present invention are substantially pure all Sp or all Rp chiral phosphorothioate linkages. Such oligonucleotides are prepared via chemical or enzymatic synthesis. They are especially well suited as diagnostics, therapeutics and research reagents.

BACKGROUND OF THE INVENTION

Oligonucleotides are known to hybridize to single-stranded RNA or single-stranded DNA. Hybridization is the sequence-specific base pair hydrogen bonding of bases of the oligonucleotides to bases of target RNA or DNA. Such base pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (°C) at which 50% helical (hybridized) versus coil (unhybridized) forms are present. $T_m$ is measured by using the UV spectrum to determine the formation and breakdown (melting) of the hybridization complex. Base stacking which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides can be used to effect enzymatic cleavage of a target RNA by using the intracellular enzyme RNase H. The mechanism of such RNase H cleavage requires that a 2'-deoxyribofuranosyl oligonucleotide hybridize to a target RNA. The resulting DNA-RNA duplex activates the RNase H enzyme and the activated enzyme cleaves the RNA strand. Cleavage of the RNA strand destroys the normal function of the target RNA. Phosphorothioate and phosphorodithioate oligonucleotides are known to operate via this type of mechanism. However, for a DNA oligonucleotide to be useful for cellular activation of RNase H, the oligonucleotide must be reasonably stable to nucleases in order to survive in a cell for a time period sufficient for RNase H activation. For non-cellular uses, such as use of oligonucleotides as research reagents, such nuclease stability may not be necessary.

Several publications of Walder et al. describe the interaction of RNase H and oligonucleotides. Of particular interest are: (1) Dagle et al., *Nucleic Acids Research* 1990, 18, 4751; (2) Dagle et al., *Antisense Research And Development* 1991, 1, 11; (3) Eder et al., *J. Biol. Chem.* 1991, 266, 6472; and (4) Dagle et al., *Nucleic Acids Research* 1991, 19, 1805. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, the authors further note that in *Xenopus embryos*, both phosphodiester linkages and phosphorothioate linkages are also subject to exonuclease degradation. Such nuclease degradation is detrimental since it rapidly depletes the oligonucleotide available for RNase H activation.

As described in references (1), (2) and (4), to stabilize oligonucleotides against nuclease degradation while still providing for RNase H activation, 2'-deoxy oligonucleotides having a short section of phosphodiester linked nucleotides positioned between sections of phosphoramidate, alkyl phosphonate or phosphotriester linkages were constructed. While the phosphoamidate-containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such a decrease in the $T_m$ value is indicative of a decrease in hybridization between the oligonucleotide and its target nucleic acid strand.

Phosphorodithioates are achiral and anionic mimics of natural DNA. They are known to hybridize to complementary DNA or RNA strands, and have demonstrated high nuclease stability. Phosphorodithioates have been shown to be modulators of gene expression and inhibitors of viral reverse transcriptase [Beaton et al., Oligonucleotides and Analogues. A Practical Approach, IRL Press, Oxford, p. 109, 1991; Beaton et al., *Tetrahedron*, 47:2377 (1991); and Bjergarde and Dahl, *Nucleic Acids Res.*, 19:5843 (1991)]. Phosphorodithioates have also been shown to induce RNase H activity in Hela cell nuclear extracts [Caruthers et al., *Nucleosides and Nucleotides*, 10:47 (1991)].

Applications of oligonucleotides as diagnostics, research reagents, and therapeutic agents require that the oligonucleotides be transported across cell membranes or taken up by cells, appropriately hybridize to target RNA or DNA, and subsequently terminate or disrupt nucleic acid function. These critical functions depend partly on the initial stability of oligonucleotides towards nuclease degradation. Further, these functions depend on specificity of the oligonucleotide for a target DNA or RNA molecule.

A serious deficiency of oligonucleotides for these purposes is their susceptibility to enzymatic degradation by a variety of ubiquitous nucleases which may be intracellularly and extracellularly located. Unmodified, "wild type", oligonucleotides are not useful as therapeutic agents because they are rapidly degraded by nucleases. Therefore, modification of oligonucleotides for conferring nuclease resistance on them has been the primary focus of research directed towards the development of oligonucleotide therapeutics and diagnostics.

Modifications of oligonucleotides to enhance nuclease resistance has generally taken place on the sugar phosphate backbone, particularly on the phosphorous atom. Phosphorothioates have been reported to exhibit resistance to nucleases. In addition, phosphorothioate oligonucleotides are generally more chemically stable than natural phosphodiester oligonucleotides. Phosphorothioate oligonucleotides also exhibit solubility in aqueous media. Further, phosphorothioate oligonucleotide-RNA heteroduplexes can serve as substrates for endogenous RNase H. Additionally, phosphorothioate oligonucleotides exhibit high thermodynamic stability. However, while the ability of an oligonucleotide to bind to a target DNA or RNA with fidelity is critical for its hybridization to the target DNA or RNA, modifications at the phosphorous atom of the oligonucleotides, while exhibiting various degrees of nuclease resistance, have generally suffered from inferior hybridization properties [Cohen, J. S., Ed., Oligonucleotides:Antisense Inhibitors of Gene Expression (CRC Press, inc., Boca Raton, Fla., 1989].

One reason for this inferior hybridization may be the prochiral nature of the phosphorous atom. Modifications on the internal phosphorous atom of modified phosphorous oligonucleotides results in Rp and Sp stereoisomers. Modified phosphorus oligonucleotides obtained thus far, wherein the resulting molecule has nonsymmetrical substituents, have been racemic mixtures having $2^n$ isomers, with n equal to the number of phosphorothioate intersugar linkages in the oligonucleotide. Thus, a 15-mer phosphorothioate oligonucleotide, containing 14 asymmetric centers has $2^{14}$ or 16,384 diastereomers. In view of this, in a racemic mixture, only a small percentage of the oligonucleotides are likely to specifically hybridize to a target mRNA or DNA with sufficient affinity.

Chemically synthesized phosphorothioate oligonucleotides having chirally pure intersugar linkages had thus far been limited to molecules having only one or two diastereomeric intersugar linkages. Until recently, the effects of induced chirality in chemically synthesized racemic mixtures of sequence-specific phosphorothioate oligonucleotides had not been assessed since synthesis of oligonucleotides having chirally pure intersugar linkages had yet to be accomplished by automated synthesis. This was due to the non-stereospecific incorporation of sulfur during automated synthesis. For example, Stec et al., J. Chromatography, 326:263 (1985), synthesized certain oligonucleotide phosphorothioates having racemic intersugar linkages, however, they were able to resolve only the diastereomers of certain small oligomers having one or, at most, two diastereomeric phosphorous intersugar linkages.

However, Stec et al. [Nucleic Acids Res., 19:5883 (1991)] subsequently reported the automated stereocontrolled synthesis of oligonucleotides. The procedure described in the above-mentioned reference utilizes base-catalyzed nucleophilic substitution at a pentavalent phosphorothioyl center.

The synthesis of phosphorothioates having all Rp intersugar linkages using enzymatic methods has been investigated by several authors [Burgers and Eckstein, J. Biological Chemistry, 254:6889 (1979); Gupta et al., J. Biol. Chem., 256:7689 (1982); Brody and Frey, Biochemistry, 20:1245 (1981); and Eckstein and Jovin, Biochemistry, 2:4546 (1983)]. Brody et al. [Biochemistry, 21:2570 (1982)]and Romaniuk and Eckstein, [J. Biol. Chem., 257:7684 (1982)]enzymatically synthesized poly TpA and poly ApT phosphorothioates, while Burgers and Eckstein [Proc. Natl. Acad. Sci. U.S.A., 75:4798 (1978)]enzymatically synthesized poly UpA phosphorothioates. Cruse et al. [J. Mol. Biol., 192:891 (1986)]linked three diastereomeric Rp GpC phosphorothioate dimers via natural phosphodiester bonds into a hexamer.

The relative ability of an oligonucleotide to bind to complementary nucleic acids may be compared by determining the melting temperature of a particular hybridization complex. The melting temperature ($T_m$), a characteristic physical property of double helixes, denotes the temperature (°C.) at which 50% helical versus coil (unhybridized) forms are present. $T_m$ is measured by using the UV spectrum to determine the formation and breakdown (melting) of hybridization. Base stacking which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$.

In a preliminary report [Stec, J. W., Oligonucleotides as Antisense Inhibitors of Gene Expression: Therapeutic Implications, Meeting abstracts, Jun. 18–21, 1989], thymidine homopolymer octamers having all but one linkage being modified phosphate linkages ("all except one") Rp stereoconfiguration or "all except one" Sp stereoconfiguration in the intersugar linkages were formed from two thymidine methylphosphonate tetrameric diastereomers linked by a natural phosphodiester bond. It was noted that a Rp "all except one" methylphosphonate non-sequence-specific thymidine homooctamer, i.e. $(dT)_8$ having all but one Rp intersugar linkage, formed a thermodynamically more stable hybrid (Tm 38° C.) with a 15-mer deoxyadenosine homopolymer, i.e. $(dA)_{15}$, than a hybrid formed by a similar thymidine homopolymer having "all except one" Sp configuration methylphosphonate linkages and of $d(A)_{15}$ (Tm<0° C.), i.e. a $d(T)_{15}$ having all but one Sp intersugar linkage. A hybrid between $(dT)_8$ having natural phosphodiester linkages, i.e. octathymidylic acid, and $d(A)_{15}$ was reported to have a Tm of 14° C.

More recently, Ueda et al. [Nucleic Acids Research, 19:547 (1991)]enzymatically synthesized mRNAs intermittently incorporating Rp diastereomeric phosphorothioate linkages for use in translation systems. Ueda et al. employed T7 coliphane DNA having seventeen promoters and one termination site for T7 RNA polymerase. In vitro synthesis by T7 RNA polymerase produced mRNAs having from several hundred to tens of thousands of nucleotides.

Backbone chirality may also affect the susceptibility of a phosphorothioate oligonucleotide-RNA heteroduplex to RNase H activity. The ability to serve as a template for RNAse H has significant therapeutic implications since it has been suggested that RNAse H causes cleavage of the RNA component in an RNA-DNA oligonucleotide heteroduplex. With oligonucleotides containing racemic mixtures of Rp and Sp intersugar linkages, it is not known if all phosphorothioate oligonucleotides can function equally as substrates for RNase H. For a variety of catalytic reactions, hydrolysis of the phosphodiester backbone of nucleic acids proceeds by a stereospecific mechanism (an in-line mechanism) and inversion of configuration. Therefore, there may be only a small percentage of oligonucleotides in a racemic mixture that contain the correct chirality for maximum hybridization efficiency and termination of translation. Thus, increasing the percentage of phosphorothioate oligonucleotides that can serve as substrates for RNAse H in a heteroduplex will likely lead to a more efficacious compound for antisense therapy.

To enhance hybridization fidelity, phosphorothioate oligonucleotides having substantially chirally pure intersugar linkages are greatly desired. Further, such phosphorothioate oligonucleotides having substantially chirally pure intersugar linkages would lead to more efficacious therapeutic compounds. However, until now little success has been achieved in synthesizing such molecules. Therefore, simple methods of synthesizing phosphorothioate oligonucleotides having substantially chirally pure intersugar linkages are greatly desired.

It has been recognized that nuclease resistance of oligonucleotides and fidelity of hybridization are of great importance in the development of oligonucleotide therapeutics. Oligonucleotides possessing nuclease resistance are also desired as research reagents and diagnostic agents.

OBJECTS OF THE INVENTION

It is an object of this invention to provide sequence-specific phosphorothioate oligonucleotides having substantially chirally pure, either all Rp or all Sp, intersugar linkages.

It is a further object of this invention to provide phosphorothioate oligonucleotides having all Rp or all Sp intersugar linkages that are specifically hybridizable to target DNA or RNA.

It is a still further object of this invention to provide methods for synthesis of sequence-specific phosphorothioate oligonucleotides having substantially chirally pure intersugar linkages.

It is another object of this invention to provide sequence-specific phosphorodithioate oligonucleotides that are specifically hybridizable to target DNA or RNA.

These and other objects of the present invention shall become apparent to persons skilled in the art to which this invention pertains given this specification and the claims appended hereto.

SUMMARY OF THE INVENTION

In accordance with this invention, phosphorothioate and phosphorodithioate oligonucleotides are provided. The phosphorothioate oligonucleotides of the invention have all nucleoside units joined together by either substantially all Sp phosphorothioate intersugar linkages or substantially all Rp phosphorothioate intersugar linkages. Preferably, the oligonucleotides of the present invention are complementary to at least a portion of the sequence of a target RNA or DNA.

In accordance with the present invention, a chemical method for the synthesis of phosphorodithioate oligonucleotides is provided. Preferably, the phosphorodithioate oligonucleotides of the invention are comprised of about 6 to about 50 nucleoside units linked together by intersugar linkages. More preferably, said phosphorodithioate oligonucleotides are comprised of about 6 to about 21 nucleoside units linked together by intersugar linkages. Most preferably, said phosphorodithioate oligonucleotides of the invention are comprised of about 8 nucleoside units linked together by intersugar linkages.

Further, in accordance with the present invention, chemical and enzymatic methods of synthesizing sequence-specific phosphorothioate oligonucleotides having substantially chirally pure intersugar linkages are provided wherein said phosphorothioate oligonucleotides are comprised of at least 6 nucleoside units joined together by either substantially all Rp or substantially all Sp intersugar linkages. Preferably, the phosphorothioate oligonucleotides are comprised of about 6 to about 50 nucleoside units joined by substantially chirally pure intersugar linkages. More preferably, said phosphorothioate oligonucleotides are comprised of about 6 to about 21 nucleoside units joined by substantially chirally pure intersugar linkages. Most preferably, said phosphorothioate oligonucleotides are comprised of about 8 nucleoside units joined together by substantially chirally pure intersugar linkages. Said methods comprise combining sequence primers, templates, and an excess of all four chirally pure nucleoside 5'-O-(1-thiotriphosphates). Said methods further include synthesizing complementary oligonucleotides by the addition of polymerase followed by cleavage of the primer from the complementary oligonucleotides. In addition, said methods are comprised of disassociating said complementary oligonucleotides from said template.

In alternative embodiments of the present invention methods of synthesizing sequence-specific phosphorothioate oligonucleotides having substantially chirally pure intersugar linkages, sequence primers, templates and racemic mixtures of nucleoside 5'-O-(1-thiotriphosphates) are combined. Phosphorothioate oligonucleotides having substantially chirally pure intersugar linkages and which are complementary to the template are synthesized by the addition of polymerase and a selected metal ion. Oligonucleotides thus synthesized are dissociated from the template and primer.

Phosphorothioate oligonucleotides having substantially chirally pure intersugar linkages are useful for increasing the thermodynamic stability of heteroduplexes formed with target RNA and DNA. The oligonucleotides of the invention are known to elicit RNase H activity. Further, oligonucleotides of the present invention are also useful for modulating the activity of RNA.

DETAILED DESCRIPTION OF THE INVENTION

The phosphorous atom in a phosphodiester linkage of an oligonucleotide can be described as being "pro-chiral." Once a non-bonding oxygen atom of the phosphodiester linkage is replaced or modified, a chiral sugar-phosphate linkage is generated. The resulting intersugar linkage is either an Sp intersugar linkage or an Rp intersugar linkage. Replacement of a non-bonding oxygen atom of the natural phosphodiester linkage with sulfur to obtain a phosphorothioate linkage results in the generation of a chiral center and affords Sp and Rp diastereomers. Molecules wherein substantially all of the phosphorous atoms in the sugar backbone are either Sp or Rp are referred to herein as chirally pure.

Ribonucleoside- (NTPαS) and 2'-deoxyribonucleoside-5'-O-(1-thiotriphosphates) (dNTPαS) have been synthesized as Sp and Rp racemic mixtures using the methodology of Ludwig and Eckstein [*J. Org. Chem.*, 631 (1989)]. In this exemplary synthetic scheme, unprotected nucleosides can be reacted with 2-chloro-4H-1,3,2-benzodioxaphosphorin-4-one, which phosphitylates the 5'-hydroxyl group. Subsequent reaction with pyrophosphate yields cyclic triphosphate derivatives which are reactive to sulfur, yielding mixtures of Rp and Sp nucleoside 5'-O-(1-thiotriphosphates), i.e. α-thiotriphosphates. The products can be purified by DEAE-Sephadex chromatography and identified by NMR spectroscopy (by characteristic Rp or Sp chemical shifts).

As is shown in the examples below, pure Rp and Sp nucleoside-5'-O-(1-thiotriphosphates) diastereomers can be readily isolated on a preparative scale using, for example, reverse phase HPLC chromatography. Such HPLC-isolated nucleotide diastereomers can be further characterized by analytical HPLC comparisons with commercial samples of such Rp and Sp nucleoside 5'-O-(1-thiotriphosphates) diastereomers.

Enzymatic synthesis of sequence-specific natural oligonucleotides, i.e. natural phosphodiester oligonucleotides, can be effected by the use of an appropriate nuclease in the presence of a template and primer. In a like manner, racemic mixtures of phosphorothioate oligonucleotides having chirally mixed intersugar linkages can be synthesized. According to the present invention, such enzymatic synthesis can also be expanded to include the synthesis of sequence specific phosphorothioate oligonucleotides having substantially chirally pure intersugar linkages by utilizing enantiomerically pure all-Sp or all-Rp nucleoside 5'-O-(1-thiotriphosphates) as substrates for appropriate nucleases in the presence of a sequence-specific template and a primer. For example, commercially available DNA polymerase Sequenase™ (U.S. Biochemical, Inc., Cleveland, Ohio) may be used to synthesize phosphorothioate oligonucleotides using a phosphodiester oligonucleotide template and a racemic phosphorothioate oligonucleotide primer. Using this polymerase both phosphodiester and phosphorothioate primers may be extended.

Yields of enzymatically synthesized phosphorothioate oligonucleotides can be optimized by repetitive additions of template and primer, by repetitive additions of polymerase, by repetitive additions of nucleoside triphosphates or by combinations of some or all of these. For instance, repetitive additions of template and primer results in maximizing yields via an enzymatic cascade. Further optimization can be achieved by pre-hybridization of template and primer together in system buffer, followed by cooling and addition of nucleoside triphosphates and polymerase.

A suitable polymerase may be selected to yield either DNA or RNA phosphorothioate oligonucleotides. Such polymerases include but are not necessarily limited to T7 DNA polymerase, modified T7 DNA polymerases such as the above referenced Sequenase™, E. coli DNA polymerase, DNA poly Klenow fragment polymerase, M. luteus polymerase, T4 bacteriophage polymerase, modified T4 DNA polymerase, T7 RNA polymerase and E. coli RNA polymerase.

The enzymatic synthesis proceeds with inversion of configuration about the chiral center of the phosphorous atom. Thus, use of all Sp α-thiotriphosphates yields substantially all Rp phosphorothioate oligonucleotides while use of all Rp α-thiotriphosphates yields substantially all Sp phosphorothioate oligonucleotides. In an alternate embodiment of the invention, phosphorothioate oligonucleotides may be synthesized from racemic mixtures of nucleoside-5'-O-(1-thiotriphosphates) utilizing metal ions in reaction solutions to promote preferential incorporation of one or the other of the chiral α-thiotriphosphates. As noted above, polymerase synthesis of phosphorothioate oligonucleotides is accomplished with inversion of configuration about the chiral center of the precursor nucleoside-α-thiotriphosphate. While not wishing to be bound by theory, it is believed that optimization of an all Rp conformation may be accomplished by addition of a high concentration of magnesium ion in the reaction buffer utilizing, for instance, an E. coli polymerase. In a like manner, again while not wishing to be bound by theory, an all Sp configuration might be obtained by utilizing a high manganese ion concentration in the reaction buffer.

In accordance with the present invention, "substantially all" is meant to include all oligonucleotides in which at least 75% of the intersugar linkages are chirally pure. More preferably, oligonucleotides having from about 85% to about 100% chirally pure intersugar linkages are substantially chirally pure. Most preferably, oligonucleotides having from about 95% to about 100% chirally pure intersugar linkages are substantially chirally pure.

In the context of this invention, the term "phosphorothioate oligonucleotide" includes phosphorothioate oligonucleotides formed from naturally occurring bases, sugars and phosphorothioate linkages. To the extent that nucleoside-5'-O-(1-thiotriphosphate) analogs are substrates for suitable polymerases, "phosphorothioate oligonucleotides" also include modified bases or modified sugars incorporated within the phosphorothioate nucleotide units of the oligonucleotides.

In the context of this invention, the term "phosphorodithioate oligonucleotide" includes phosphorodithioate oligonucleotides formed from naturally occurring bases, sugars and phosphorodithioate linkages. The term "phosphorodithioate oligonucleotides" may also include modified bases or modified sugars incorporated within the phosphorodithioate nucleotide units of the oligonucleotides.

Naturally occurring bases include adenine, guanine, cytosine, thymine and uracil. Natural sugars include β-D-ribofuranosyl and β-D-2'-deoxy-erythro-pentofuranosyl. Modified bases of the oligonucleotides of this invention include adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The oligonucleotides of the invention may also comprise modified nucleobases or nucleobases having other modifications consistent with the spirit of this invention, and in particular modifications that increase their nuclease resistance in order to facilitate their use as therapeutic, diagnostic or research reagents.

Oligonucleotides of the invention can be utilized as diagnostics, therapeutics and as research reagents. They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 µg to 100 g per kg of body weight depending on the age of the patient and the severity of the disease state being treated. Further, the treatment regimen may last for a period of time which will vary depending upon the nature of the particular disease, its severity and the overall condition of the patient, and may extend from once daily to once every several years. Following treatment, the patient is monitored for changes in his/her condition and for alleviation of the symptoms of the disease state. The dosage of the oligonucleotide may either be increased in the event the patient does not respond significantly to current dosage levels, or the dose may be decreased if an alleviation of the symptoms of the disease state is observed, or if the disease state has been ablated.

In some cases it may be more effective to treat a patient with an oligonucleotide of the invention in conjunction with other traditional therapeutic modalities. For example, a patient being treated for AIDS may be administered an oligonucleotide in conjunction with AZT.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every several years.

Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Phosphorothioate oligonucleotides of the present invention can be contrasted with both natural phosphodiester oligonucleotides and racemic phosphorothioate nucleotides as to their effects on hybridization, nuclease resistance and RNAse H activity. In like manner, pure phosphorothioate oligonucleotides having substantially chirally pure intersugar linkages may also be assessed for their ability to increase effectiveness of therapy in in vivo test systems. Such increase in effectiveness of therapy might include attributes such as pharmacokinetics or metabolism, toxicology, disposition (i.e. absorption and distribution), and species comparisons.

Homopolymers having all Rp or all Sp intersugar linkages have been useful for initial studies of stability and other characteristics. However, these oligonucleotides have little use therapeutically as they are not specific for target molecules. Phosphorothioate oligonucleotides having specific sequences are necessary in order to specifically hybridize to target nucleic acids.

Sequence-specific phosphorothioate oligonucleotides having substantially chirally pure intersugar linkages are useful to increase the thermodynamic stability of heteroduplexes with target RNA and DNA and to elicit RNase H activity.

Radiolabeling can be used to assist in the identification of phosphorothioate oligonucleotides having substantially chirally pure intersugar linkages. For racemic phosphorothioate oligonucleotides synthesized on an automated synthesizer, [$^{35}$S] (radiolabeled elemental sulfur) can be used for oxidation of the hydrogen-phosphonate oligomers obtained from the synthesizer. Labeling of enzymatically synthesized phosphorothioate oligonucleotides can be accomplished with [$\alpha$-$^{32}$P]ATP and ligase or [$\alpha$-$^{35}$S]ATPs in the polymerase reaction. Also, radiolabeled nucleoside triphosphates can be used in probe and sequencing analysis. Autoradiograms are prepared in standard manners.

Templates of the present invention are most preferably areas of nucleic acid sequence which direct synthesis of disease-potentiating proteins. Short oligonucleotides that base pair to a region of said template oligonucleotide act as primers which form the starting point for oligonucleotide synthesis by polymerases.

Phosphorothioate oligonucleotides having substantially chirally pure intersugar linkages may be synthesized using a primer which may be selected to have a site thereon that is susceptible to nuclease cleavage, for example, restriction endonuclease cleavage. Said cleavage site may be located at the 3' end of said primer. Cleavage at said site by an appropriate restriction endonuclease results in oligonucleotides deriving a first 5' end nucleoside from said primer. Additional nucleosides of said phosphorothioate oligonucleotides of the present invention are those nucleoside chiral thiotriphosphates added via enzymatic means.

By selecting appropriate restriction nucleases in conjunction with selected primers, various 5'-terminal nucleosides of desired phosphorothioate oligonucleotides are appropriately positioned at the 5' end of a phosphorothioate nucleotide. Thus, any endonuclease recognition site can be designed as long as the staggered cut results in one nucleoside from the primer being the first 5' nucleoside of the newly synthesized sequence specific phosphorothioate oligonucleotide of the invention. This results in the generation of different nucleosides on 5' ends of enzymatically synthesized phosphorothioate oligonucleotides of the invention.

Upon completion of enzymatic extension of said primer on an appropriate template of a desired sequence, phosphorothioate oligonucleotides of the invention may be released from said primer by use of appropriate nuclease. For example, for incorporation of a guanosine nucleoside at the 5' end of desired phosphorothioate oligonucleotides, a primer having an CTGCAG sequence at its 3' terminal end may be used. Use of a Pst 1 restriction nuclease then may cleave the A–G linkage. The guanosine nucleoside component of this A–G linkage may thus incorporated as a 5' terminal nucleoside of desired phosphorothioate oligonucleotides. Other restriction endonuclease include but are not limited to BamH1, Smal and HinD III restriction endonucleases.

Oligonucleotides still associated with said template may be dissociated from said template and then purified by gel electrophoresis and/or chromatography. For example, suitable purification can be accomplished utilizing standard polyacrylamide/urea gel electrophoresis coupled with Sep-Pac (Millipore, Miford, Mass.) chromatography. Another useful chromatographic technique that may be employed is HPLC chromatography.

Chiral phosphorothioate oligonucleotides of the present invention may also be chemically synthesized via 1,3,2-oxathiaphospholane intermediates as described by Stec et al. [*Nucleic Acids Res.*, 19:5883 (1991)]and Stec and Lesnikowski [Methods in Molecular Biology, S. Agrawal, Ed., Volume 20, p. 285, 1993].

Phosphorodithioate oligonucleotides of the invention may be synthesized by automated solid phase synthesis using nucleoside phosphorothiamidites according to the procedure of Dahl et al. [*Acta Chem. Scand.*, 43:896 (1989)]and Caruthers et al. [U.S. Pat. No. 5,278,302].

Phosphorothioate oligonucleotides having substantially chirally pure intersugar linkages which are synthesized according to methods of the present invention may be analyzed by a number of methods. For example, configuration analysis of resulting sequence-specific phosphorothioate oligonucleotides having substantially chirally pure all Sp or all Rp intersugar linkages may be determined by the use of [$^{31}$P] NMR chemical shifts. Such chemical shifts have been used to identify the Rp epimer of a phosphorothioate dinucleotide [Ludwig and Eckstein, *J. Org. Chem.*, 631–635 (1989)].

The fidelity of sequences of phosphorothioate oligonucleotides of the invention can be determined using the sensitivities of heteroduplexes to S1 nuclease.

The sequence of the phosphorothioate oligonucleotides can be further substantiated by labeling the 3'hydroxyl groups of phosphorothioate oligonucleotides with [alpha-$^{32}$P]cordycepin triphosphate, i.e. 3'-deoxyadenosine-5'-triphosphate. The resultant oligonucleotides may be subjected to enzymatic degradation.

The relative ability of phosphorothioate oligonucleotides having substantially chirally pure intersugar linkages to bind to complementary strands is compared by determining the melting temperature of a hybridization complex of a phosphorothioate oligonucleotide having substantially chirally pure intersugar linkages and its complementary strand. The melting temperature ($T_m$), a characteristic physical property of double helices, denotes the temperature in degrees centigrade at which 50% helical versus coiled (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non Watson-Crick base pairing has a strong destabilizing effect on the $T_m$. Consequently, as close to optimal fidelity of base pairing as possible is desired to have optimal binding of an oligonucleotide to its targeted RNA.

Phosphorothioate oligonucleotides of the invention can also be evaluated for their resistance to the degradative ability of a variety of exonucleases and endonucleases. Phosphorothioate oligonucleotides may be treated with nucleases and then analyzed, as for instance, by polyacrylamide gel electrophoresis (PAGE) followed by staining with a suitable stain such as Stains All™ (Sigma Chem. Co., St. Louis, Mo.). Degradation products may be quantitated using laser densitometry.

Fetal calf and human serum may be used to evaluate nucleolytic activity on phosphorothioate oligonucleotides having substantially chirally pure intersugar linkages. For instance, a phosphorothioate oligonucleotide having substantially all Rp intersugar linkages may be evaluated in this manner. Testing on combinations of 3' or 5' end capped (having one or several phosphorothioate linkages per cap) molecules may be used to establish a combination that yields greatest nuclease stability. Capping can be effected by chemically synthesizing the cap portion of a sequence using purified Rp monomers followed by incorporation of said cap into oligonucleotides on the DNA synthesizer. Analysis involving capping can determine the importance of chirality on nucleolytic stability and the number of linkages required to obtain maximum stability.

The sensitivity of phosphorothioate oligonucleotide-RNA heteroduplexes to the catalytic activity of RNase H can also be assessed. A phosphorothioate oligonucleotide can be incubated with a radiolabeled target mRNA (synthesized as for instance via T7 RNA polymerase) at various temperatures for hybridization. Heteroduplexes can then be incubated at 37° C. with RNase H from *E. coli* according to the procedure of Minshull and Hunt [*Nuc. Acid Res.*, 6433 (1986)]. Products may then be assessed for RNase H activity by Northern Blot analysis wherein products are electrophoresed on a 1.2% agarose/formaldehyde gel and transferred to nitrocellulose. Filters may then be probed using a random primer [$^{32}$P]-labeled cDNA complementary to target mRNA and quantitated by autoradiography. Comparisons between different phosphorothioate analogs can be made to determine the impact of chirality on the ability to act as a substrate for RNase H when complexed to RNA.

Comparisons of the susceptibility of heteroduplexes to the catalytic action of *E. coli* RNase H and mammalian RNAse H can be performed. Heteroduplexes can be incubated in rabbit reticulocyte lysates under conditions of translation and assayed via Northern blot analysis for catalytic cleavage of mRNA by endogenous RNase H. This allows for determination of the effects of chirality on mammalian RNAse H activity.

Phosphorothioate oligonucleotides having substantially chirally pure intersugar linkages can also be evaluated for inhibition of gene expression in cell culture model systems. To determine if a phosphorothioate oligonucleotide having substantially pure chirally pure intersugar linkages is more potent or a more specific inhibitor of gene expression, a phosphorothioate oligonucleotide having substantially chirally pure intersugar linkages designed to target reporter genes may be synthesized and tested in cell culture models of gene expression. The use of the vector pSV2CAT has previously been described to measure antisense effects on gene expression [Henthorn et al., *Proc.Natl.Acad. Sci. U.S.A.*, 85:6342 (1988)]. This vector contains the bacterial chloramphenicol acetyl transferase gene under regulatory controls of the SV40 promoter. Utilizing a 15-mer phosphorothioate oligonucleotide having all Rp intersugar linkages of a sequence complementary to the initiation of translation of the CAT mRNA, pSV2CAT may be transfected into HeLa cells and, following treatment of the cells for 48 hr with a phosphorothioate oligonucleotide having all Rp intersugar linkages, CAT activity may then be assayed in the cells. The activity of a phosphorothioate having substantially chirally pure intersugar linkages in inhibition of gene expression may then be compared directly with a chemically synthesized random phosphorothioate having diastereomeric intersugar linkages and natural phosphodiester oligonucleotides of the same sequence.

The vector pSV2APAP [Marcus-Sekura et al., *Nucleic Acids Research*, 15:5749 (1987)] contains the mammalian placental alkaline phosphatase gene (PAP). This can also be used as a reporter for measuring antisense effects on gene expression. PAP has advantages over CAT as a reporter gene in that it is a mammalian gene, rather than a bacterial gene that contains introns and other RNA processing signals. It is presently believed that PAP expression mimics more closely the events in natural mammalian gene expression. A 15-mer phosphorothioate oligonucleotide having substantially chirally pure intersugar linkages as described above for the CAT mRNA can be examined in parallel with chemically synthesized racemic phosphorothioate and natural phosphodiester oligonucleotides having similar sequences. The PAP and CAT reporter constructs are used as controls in reciprocal experiments to test for non-specific effects on gene expression.

Additionally, phosphorothioate oligonucleotides having substantially chirally pure intersugar linkages can be evaluated as to their ability to act as inhibitors of RNA translation in vivo. Various therapeutic areas can be targeted for such manipulation by oligonucleotides of the present invention. One such therapeutic area includes AIDS and other related infections mediated by HIV. ISIS-5320 is a phosphorothioate oligonucleotide having application in the treatment of AIDS, and has the sequence TTGGGGTT (SEQ ID NO:1). In the above sequence, individual nucleotide units of the oligonucleotide are listed in a 5' to 3' direction from left to right.

In the context of this invention, "hybridization" shall mean hydrogen bonding, which may be Watson-Crick, Hoogsteen or reversed Hoogsteen hydrogen bonding, between complementary nucleotide units. For example, adenine and thymine are complementary nucleobases which pair through the formation of hydrogen bonds. "Complementary," as used herein, also refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotide units which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

In particular, oligonucleotides of the invention may be used in therapeutics, as diagnostics, and for research as is specified in the following United States patent applications assigned to the assignee of this invention These applications are entitled: Compositions and Methods for Modulating RNA Activity, U.S. Ser. No. 463,358, filed Jan. 11, 1990; Antisense Oligonucleotide Inhibitors of Papilloma Virus, U.S. Ser. No. 445,196 Filed Dec. 4, 1989; Oligonucleotide Therapies for Modulating the Effects of Herpesvirus, U.S. Ser. No. 485,297, Filed Feb. 26, 1990; Reagents and Methods for Modulating Gene Expression Through RNA Mimicry U.S. Ser. No. 497,090, Filed Mar. 21, 1990; Oligonucleotide Modulation of Lipid Metabolism, U.S. Ser. No. 516,969, Filed Apr. 30, 1990; Oligonucleotides for Modulating the Effects of Cytomegalovirus infections, U.S. Ser. No. 568,366, Filed Aug. 16, 1990; Antisense Inhibitors of the Human Immunodeficiency Virus, U.S. Ser. No. 521,907, Filed May 11, 1990; Nuclease Resistant Pyrimidine Modified Oligonucleotides for Modulation of Gene Expression, U.S. Ser. No.558,806, Filed Jul. 27, 1990; Novel Polyamine Conjugated Oligonucleotides, U.S. Ser. No. 558,663, Filed Jul. 27, 1990; Modulation of Gene Expression Through Interference with RNA Secondary Structure, U.S. Ser. No. 518,929, Filed May 4, 1990; Oligonucleotide Modulation of Cell Adhesion, U.S. Ser. No. 567,286, Filed Aug. 14, 1990; Inhibition of Influenza Viruses, U.S. Ser. No. 567,287, Filed Aug. 14, 1990; Inhibition of Candida, U.S. Ser. No. 568,672, Filed Aug. 16, 1990; and Antisense Oligonucleotide Inhibitors of Papillomavirus, U.S. Ser. No. PCT/US90/07067, Filed Dec. 3, 1990. These applications disclose a number of means whereby improved modulation of RNA and DNA activity may be accomplished through oligonucleotide interaction. In that the specific sequences disclosed therein may be used in conjunction with the present invention, the disclosures of the foregoing United States patent applications are incorporated herein by reference.

The following examples are illustrative and are not meant to be limiting of the present invention.

EXAMPLE 1

ISOLATION OF ALL Sp OR ALL Rp 5'-O-(1-THIOTRIPHOSPHATE) NUCLEOSIDE

5'-O-(1-thiotriphosphate) deoxynucleosides and ribonucleosides are isolated using C-18 reverse phase high performance liquid chromatography (HPLC) using columns packed with ODS Hypersil (Shahdon Southern, Runcon, UK) and eluted with an isocratic mixture of solvent A (30 mM potassium phosphate containing 5mM tetrabutylammonium ion, pH 7.0) and solvent B (5 mM tetrabutylammonuium hydroxide in methanol). Alternatively, effective separation is achieved using 100 mM triethylammonium bicarbonate, pH 7.5, containing a linear gradient of acetonitrile from 0% to 15% over 20 minutes.

To establish the purity of such HPLC separated enantiomers the HPLC separated Sp and Rp deoxynucleotide enantiomers are compared to commercially available deoxynucleoside 5'-O-(1-thiotriphosphates) available from E.I. Dupont, Wilmington, Del.

EXAMPLE 2

SYNTHESIS OF PHOSPHOROTHIOATE EXTENSION HAVING SUBSTANTIALLY ALL Rp INTERSUGAR LINKAGES OF A RACEMIC PHOSPHOROTHIOATE OLIGONUCLEOTIDE

Enzymatic synthesis of an all Rp phosphorothioate extension of a racemic phosphorothioate oligonucleotide primer is effected using the modified T7 DNA polymerase I, Sequenase™ (U.S. Biochemicals Corp, Cleveland, Ohio). This T7 DNA polymerase is used to extend an 18 mer phosphorothioate oligonucleotide primer hybridized to a 21-mer natural phosphodiester oligonucleotide. 30 picomoles (pmol) of primer and template in a 1X Sequenase™ reaction buffer (U.S. Biochemicals Corp., Cleveland, Ohio) (final vol 10 µL) are heated for 5 minutes at 95° C. and slowly cooled to room temperature. 180 pmol of deoxy 5'-[α-$^{35}$S]cytidine triphosphate and Sequenase™ enzyme (U.S. Biochemicals Corp., Cleveland, Ohio) are added and incubated at 37° C. for 20 minutes. The product is analyzed via polyacrylamide gel electrophoresis (PAGE) using a 20% polyacrylamide/7M urea denaturing gel. The autoradiograph of the product is compared to a control reaction absent primer/template. The final product is subjected to further characterization by, for example, enzymatic degradation. One such degradation is snake venom phosphatase degradation. A snake venom phosphatase degradation of dinucleoside monophosphorothioate synthesized using E. coli DNA polymerase I shows the dinucleoside to be of the Rp configuration.

EXAMPLE 3

SYNTHESIS OF PHOSPHOROTHIOATE CGACTATGCAAGTAC (SEQ ID NO:2) OLIGONUCLEOTIDE HAVING SUBSTANTIALLY PURE RP INTERSUGAR LINKAGES

A large scale enzymatic synthesis of sequence specific all Rp phosphorothioate oligonucleotide was effected utilizing a 55-met natural phosphodiester template and a 41-mer natural phosphodiester primer. The template sequence was GTACTTGCATAGTCGATCGGAAAAT-AGGGTTCTCATCTCCCGGGATTTGGTTGAG (SEQ ID NO: 3). The primer sequence was CTCAACCAAATC-CCGGGAGATGAGAACCCTATTTTCCGATC (SEQ ID NO: 4). The template was selected to have a sequence complementary to a desired specific CGACTATGCAAG-TAC (SEQ ID NO:2) sequence. A Sequenase™ buffer (U. S. Biochemicals Corp., Cleveland, Ohio) diluted from 5X to 1X was used. The template and primer, both at concentrations of 20 nM are added to 40 µL of this buffer. The template and primer were hybridized at 95° C. for 5 minutes and cooled to room temperature. After cooling the buffer was adjusted to 7 mM DTT. 20 µL of 1:8 diluted Sequenase™ enzyme and 320 µM each of Sp GTPαS, CTPαS, ATPαS and TTPαS were then added. The reaction solution was adjusted to 140 µL with H$_2$O It was incubated at 37° C. for 18 hours. The reaction solution was extracted 2X with a like volume of phenol in a standard manner and precipitated in a standard manner by treatment with 2.5 volumes of 100% ethanol at −20° C., peltitized, washed with 500 µL of 70% ethanol, peltitized again and dried. The precipitate was suspended in 20 µL H$_2$O for 30 minutes then adjusted to 1 mM CaCl$_2$, 25 mM Tris HCl pH 8.0 in 40 µL H$_2$O. The solution was maintained at 95° C. for 5 minutes and snap cooled, i.e. very quickly cooled with ice. The template and primer were removed from the synthesized oligonucleotide by the addition of 4.6 µM DNase I and incubation at 37° C. for 10 minutes. The reaction mixture was phenol extracted 2X and precipitated with ethanol as above. The precipitate was resuspended in H$_2$O and purified using 20% polyacrylamide/7M urea gel electrophoresis coupled with SepPak™ chromatography (Millipore, Milford, Mass.).

In an alternate synthesis, Pst 1 restriction nuclease (Life Technologies, Inc., Gaithersburg, Md.) was used to cleave the primer-bound phosphorothioate oligonucleotide at the restriction site. The desired CGACTATGCAAGTAC (SEQ ID NO:2) phosphorothioate oligonucleotide was purified using polyacrylamide/7M urea gel electrophoresis coupled with SepPak™ chromatography (Millipore, Milford, Mass.). Yields were optimized using enzymatic cascade effected by repetitive template-primer addition throughout the reaction. The cascade augmented synthesis yielded 75 A$_{260}$ units of the CGACTATGCAAGTAC (SEQ ID NO:2) all Rp configuration phosphorothioate oligonucleotide from a 20 mL reaction.

EXAMPLE 4

SYNTHESIS OF PHOSPHOROTHIOATE OLIGONUCLEOTIDES HAVING A RACEMIC MISTURE OF INTERSUGAR LINKAGES USING AUTOMATED DNA SYNTHESIS

Oligonucleotides are synthesized on an automated DNA synthesizer (Applied Biosystems model 380B) using hydrogenphosphonate chemistry in a standard manner [Agrawal et al., Proc. Natl. Acad. Sci. U.S.A., 85:7079 (1988)]. After the final coupling step, the phosphorothioate linkages are generated by oxidizing the bound oligomer with sulfur in carbon disulfide/triethylamine/ pyridine. After sulfur oxidation, standard deblocking procedures with ammonium hydroxide are used to release the oligonucleotides from the support and remove base blocking groups. The phosphorothioate oligonucleotides are purified by oligonucleotide purification column (OPC; ABI, Foster City, Calif.) chromatography and HPLC, using a Beckman System Gold HPLC. The HPLC-purified oligonucleotides are then precipitated with ethanol and assessed for final purity by gel electrophoresis on 20% acrylamide/7M urea or by analytical HPLC. The authenticity of the oligonucleotide sequence was assessed by oxidation with iodine in pyridine/water and standard sequencing methods. These oligonucleotides contain a mixture of all possible combinations of Rp and Sp isomers at each phosphorous linkage.

EXAMPLE 5

SYNTHESIS OF COMPLEMENTARY DNA OR RNA SEQUENCES USING T7 RNA POLYMERASE OR THERMODYNAMIC AND KINETIC HYBRIDIZATION ANALYSIS

The synthesis of short complementary DNA oligonucleotides of natural phosphodiester linkages was performed utilizing standard automated synthesis on an ABI model 380B DNA Synthesizer. The oligonucleotides of correct length were purified by HPLC and sequenced by standard techniques.

T7 RNA polymerase was use for the synthesis of short, complementary RNA oligonucleotides for hybridization analysis. A large amount of T7 RNA polymerase at high concentrations was needed for the many cycles of initiation required to synthesize short RNAso Due to this requirement, the T7 RNA polymerase was derived from a strain of E. coli that contained a T7 RNA polymerase expression vector, BL21/pAR1219, obtained from Brookhaven National Laboratory (Upton, N.Y.). The isolation yielded approximately 300,000 to 500,000 units of T7 RNA polymerase from 2 L of cells, absorbance value=1.2 A$_{600}$. This was sufficiently concentrated for synthesis of short (10–30 nucleotides) RNA species. For synthesis, a T7 promoter and a template containing the complementary target sequence and T7 promoter hybridization sequence were synthesized using the ABI synthesizer (ABI, Foster City, Calif.). Template and promoter were purified by HPLC to ensure that the correct species was present for enzymatic synthesis. Synthesized products were purified on a 20% polyacrylamide/8M urea gel and sequenced by standard procedures.

EXAMPLE 6

THERMAL DENATURATION

Oligonucleotides (either phosphorothioate oligonucleotides of the invention or otherwise) were incubated with either the complementary DNA or RNA oligonucleotides at a standard concentration of 4 µM for each oligonucleotide in 100 mM ionic strength buffer (89.8 mM NaCl, 10 mM Na-phosphate, pH 7.0, 0.2 mM EDTA). Samples were heated to 90° C. and the initial absorbance taken using a Guilford Response II spectrophotometer (Corning). Samples were then slowly cooled to 15° C. and the change in absorbance at 260 nm monitored during the heat denaturation procedure. The temperature was elevated 1 degree/absorbance reading and the denaturation profile analyzed by taking the first derivative of the melting curve. Data was also analyzed using a two-state linear regression analysis to determine the $T_m$ and delta G. The results of these tests are shown in Table 1.

TABLE 1

THERMAL DENATURATION

| Sequence | SEQ ID NO: | Complement | $T_m$ |
|---|---|---|---|
| Natural phosphodiester | | | |
| CGA CTA TGC AAG TAC | 2 | DNA | 53.2 |
| CGA CTA TGC AAG TAC | 2 | RNA | 46.2 |
| Phosphorothioate with racemic intersugar linkages | | | |
| CGA CTA TGC AAG TAC | 2 | DNA | 46.0 |
| CGA CTA TGC AAG TAC | 2 | RNA | 36.5 |
| Phosphorothioate with chirally pure intersugar linkages | | | |
| CGA CTA TGC AAG TAC | 2 | DNA | 45.5 |
| CGA CTA TGC AAG TAC | 2 | RNA | 41.5 |
| GA CTA TGC AAG TAC | 5 | DNA | 44.5 |
| GA CTA TCC AAG TAC | 5 | RNA | 40.0 |

EXAMPLE 7

SYNTHESIS OF RADIOLABELED OLIGONUCLEOTIDES

Filter binding assays are utilized to quantitate the binding stringencies of various phosphorothioate oligonucleotides, i.e. their tendencies to hybridize and form heteroduplexes with DNA or RNA. These assays require radiolabeled oligonucleotides.

Phosphorothioate oligonucleotides having all Rp intersugar linkages are synthesized by enzymatic methods from [$^{35}$S]-monomers that have been purified from Sp monomers. For automated synthesis of phosphorothioate oligonucleotides containing mixed chirality intersugar linkages, oligonucleotides are synthesized containing hydrogen phosphonates and then sulfurized in the presence of elemental [$^{35}$S] in a pyridine/carbon disulfide mixture. The resulting radiolabeled phosphorothioate oligonucleotide can be purified by OPC chromatography and HPLC. Target mRNA are applied to nitrocellulose filters and baked at 80° C. for 2 hours, blocked and then hybridized with the radiolabeled phosphorothioate oligonucleotide. Binding stringency is assessed by quantitating radiolabeled oligonucleotide eluted from the filters after increases in temperature or increases in the ionic strength of an eluting buffer, as for instance, Tris NaCl buffer. Eluted oligonucleotides are also assessed for their mobility in an anion exchange HPLC protocol isocratically utilizing phosphate buffer. Results are compared to the mobility of standard oligonucleotides prepared having racemic mixtures of intersugar linkages.

EXAMPLE 8

NUCLEASE DIGESTION

Determination of the rate of nuclease degradation of the phosphorothioate oligonucleotides in media containing 10% fetal calf serum (FCS) was carried out in Dulbecco's Modified Essential Medium (DMEM) containing 10% heat inactivated FCS. Heat inactivation of the FCS was carried out at 55° C. for 1 hour prior to addition to media. Oligonucleotides having racemic and chirally pure intersugar linkages were separately tested for resistance to nuclease digestion. 66 µg/mL of each oligonucleotide were separately added to medium and incubated at 37° C., at the time intervals indicated in Table 2. 15 µL Aliquots were removed and added to 15 µL of 9M urea in 0.1M Tris-HCl (pH 8.3), 0.1M boric acid and 2 mM EDTA. Aliquots were mixed by vortex and stored at −20° C. Polyacrylamide gel electrophoresis (PAGE) analysis was on 20% polyacrylamide/7M urea slab gels. Following electrophoresis, gels were stained using "Stains All" (Sigma Chem. Co., St. Louis, Mo.). Following de-staining, gels were analyzed via laser densitometry using an UltraScan XL device (Pharmacia LKB Biotechnology, Uppsala, Sweden). Integrations were performed and the data presented as the percentage decrease from full length (n) prior to incubation to n−1. These results are shown in Table 2 for the oligonucleotide sequence CGACTATGCAAGTAC (SEQ ID NO:2) having Rp chirally pure intersugar linkages.

TABLE 2

NUCLEASE DIGESTION
Incubation in 10% fetal calf serum
Digestion of oligonucleotide of length n to length n-1

| Time (hours) | Phosphorothioate with with racemic intersugar linkages | Phosphorothioate with chirally pure intersugar linkages |
|---|---|---|
| 0 | 0 | 0 |
| 1 | 44 | 10 |
| 2 | 45 | 10 |
| 4 | 54 | 12 |
| 24 | 70 | 44 |
| 48 | 70 | 62 |

As is evident from Table 2, the phosphorothioate oligonucleotide having substantially chirally pure intersugar linkages showed greater resistance to nuclease degradation than did the phosphorothioate oligonucleotide having racemic intersugar linkages.

EXAMPLE 9

RNASE H ANALYSIS

Phosphorothioate oligonucleotides having racemic and substantially chirally pure intersugar linkages were analyzed for susceptibility to RNase H. Oligonucleotides (2-fold molar excess to RNA) and 5 μg (3.1 kb) in vitro synthesized mRNA (using T7 RNA polymerase promoter) were incubated in 5 μL RNase H hybridization buffer for 30 minutes at 60° C. Samples were slowly cooled to room temperature and then adjusted to 3.7 mg/mL BSA, 20 units *E. coli* RNase H (Promega), 142 mMDTT, 150 mM KCl , and 3 mM MgCl$_2$. Samples were incubated for 30 minutes at 37° C. Samples were then extracted with phenol, precipitated with ethanol, and analyzed by electrophoresis on 1.2% agarose gels following ethidium bromide staining. Markers were run on gels concurrently with the samples to determine approximate length of RNA samples.

EXAMPLE 10

A patient suffering from AIDS is treated with ISIS-5320, an oligonucleotide synthesized according to Example 3 or Example 14, and having the sequence TTGGGGTT (SEQ ID NO:1). 1–1000 μg/kg body weight of oligonucleotide is incorporated into a pharmaceutically acceptable carrier and administered intravitreally. Treatment may be repeated as necessary until the infection is ablated.

Compounds 1, 2 and 3 of Examples 11, 12 and 13, respectively, are synthesized according to the procedure of Stec et al. [*Nucleic Acids Res.*, 19:5883 (1991)]and Stec and Lesnikowski [Methods in Molecular Biology, S. Agrawal, Ed., Volume 20, p. 285, 1993].

EXAMPLE 11

SYNTHESIS OF 2-CHLORO-1,3,2-OXATHIAPHOSPHOLANE (1)

A mixture of pyridine (1 mol), benzene (400 mL), 2-mercaptoethanol (0.5 mol) and phosphorus trichloride (0.5 mol) are stirred at room temperature for 30 minutes. Pyridinium chloride is filtered off, solvent is evaporated under reduced pressure and crude product is purified by distillation under reduced pressure. The fraction boiling at 70°–72° C./20 mm Hg is collected and characterized by $^{31}$P NMR.

EXAMPLE 12

SYNTHESIS OF N,N-DIISOPROPYLAMINO-1,3,2-OXATHIAPHOSPHOLANE (2)

Compound 1 (0.2 mol) is dissolved in n-pentane (300 mL) and diisopropylamine (0.4 mol) is added dropwise. The reaction mixture is stirred at room temperature for 30 minutes, after which diisopropylamine hydrochloride is filtered off, solvent is evaporated under reduced pressure and crude product is purified by vacuum distillation. Product 2 is obtained as the fraction boiling at 70° C./0.1 mm Hg and is characterized by $^{31}$P NMR and mass spectroscopy.

EXAMPLE 13

SYNTHESIS OF 5'-O-DIMETHOXYTRITYLTHYMIDINE-3'-O[2-THIONO-1,3,2-OXATHIAPHOPSHOLANE](3)

5'-O-Dimthoxytritylthymidine (10 mmol) and 1H-tetrazole (11 mmol) are vacuum dried and dissolved in dichloromethane (25 mL). Compound 2 (11 mmol) is added to the solution and the reaction mixture is stirred at room temperature for 2 hours. Dried elemental sulfur (15 mmol) is added and the reaction mixture is stirred and left at room temperature for 16 hours. Unreacted sulfur is then filtered off and the filtrate is concentrated under reduced pressure. The residue is dissolved in chloroform (3 mL) and purified by silica gel (230–400 mesh) column chromatography, eluting first with chloroform, and next with chloroform:methanol (97:3). Individual diastereomeric species of compound 3 are obtained by column chromatography on silica gel. Compound 3 is dissolved in ethyl acetate and applied on a silica gel 60H column. Ethyl acetate is used as the eluting solvent, and elution is monitored by HPTLC (silica gel 60, ethyl acetate as the developing solvent). Fractions containing separated diastereomers of compound 3 are concentrated under reduced pressure and the residue is characterized by $^{31}$P NMR and HPLC (Lichrospher Si100, 5 μM, ethyl acetate as eluant, flow rate 3 mL/minute). The fast eluting fraction corresponds to the Sp diastereomer, and the slow eluting fraction is the Rp diastereomer.

EXAMPLE 14

STEREOSPECIFIC CONTROL OF REACTION BETWEEN 5'-OH NUCLEOSIDES AND DIASTEREOMERICALLY PURE 3 IN SOLID PHASE AUTOMATED SYNTHESIS

The procedure of Stec et al. was followed using an Applied Biosystems (Foster City, Calif.) model 380B automated DNA synthesizer. The reaction between a 5'-OH nucleoside and diastereomerically pure nucleoside oxathiaphospholane, such as 3, requires the use of 1,8-diazabicyclo(5.4.0)undec-7-ene (DBU) as the catalyst. Because the commercially available linker used for the attachment of oligonucleotide to support matrix in automated DNA synthesis is unstable to DBU, a modification is required in the linker. A suitable linker for oligonucleotide synthesis via the oxathiaphospholane method is a "succinic-sarcosinyl" linker that is resistant to DBU, and can be hydrolyzed by concentrated ammonium hydroxide at room temperature in less than 1 hour.

(A) Synthesis of 5'-O-dimethoxytritylnucleosides bound to solid matrix via "succinic-sarcosinyl" linker:

(1) N-Fmoc-sarcosine (Bachem Bioscience, Inc., Philadelphia, Pa.) (1.6 mmol) is added to long chain alkyl amine-CPG (LCA-CPG, Sigma, St. Louis, Mo.) (2 g) and dried under vacuum. Anhydrous DMF (5 mL), pyridine (0.5 mL) and DCC (2.4 mmol) are added and the reaction mixture is shaken at room temperature for 12 hours. The solvent is then filtered off and the support is washed with methanol:acetonitrile:pyridine (1:1:1, 3×20 mL). The N-Fmoc protecting group is removed by treating the support with 10 mL of a 10% solution of piperidine in pyridine. N-sarcosinylated LCA-CPG is washed with methanol: acetonitrile: pyridine (1:1:1, 3×20 mL) and dried under vacuum.

(2) 5'-O-Dimethoxytritylnucleoside is added to the sarcosinylated LCA-CPG obtained as described in (1) in the presence of DMF (2 mL), pyridine (0.2 mL) and DCC (50 mg). The reaction mixture is shaken at room temperature for 12 hours and then washed with methanol: acetonitrile: pyridine (1:1:1, 3×20 mL). After drying, the support is treated with N-methylimidazole: THF (1 mL) and acetic anhydride/lutidine (1 mL) for 15 minutes. The support is then washed with methanol:acetonitrile:pyridine (1:1:1, 3×10 mL), followed by acetonitrile (3×10 mL), and then dried under vacuum.

(B) Diastereomerically pure activated nucleosides are subsequently added onto the oligonucleotide attached to the sarcosinyl LCA-CPG support in the presence of a 300-fold molar excess of DBU. The diastereomers of activated nucleosides are separated by column chromatography

[silica gel 60H, ethyl acetate is used as the eluting solvent, elution is monitored by HPTLC (silica gel 60, ethyl acetate as the developing solvent)] prior to use in the coupling reaction. The synthetic protocol is shown in Table 3.

TABLE 3

Chemical steps for one synthesis cycle

| Reagent or solvent | Purpose | Time (minutes) |
|---|---|---|
| Trichloroacetic acid in dichloromethane (2:98) | Detritylation | 1.5 |
| Acetonitrile | Wash | 2 |
| Activated nucleoside (with DBU) in acetonitrile | Coupling | 10 |
| Acetonitrile | Wash | 2 |
| Acetic anhydride/lutidine in THF (1:1:8) and N-methylimidazole in THF (4:21) | Capping | 1 |
| Acetonitrile | Wash | 1 |

The diastereomeric purity of the phosphorothioate oligonucleotide can be determined by $^{31}$P NMR, by HPLC (Lichrospher Si100, 5 μM, ethyl acetate as eluant, flow rate 3 mL/minute), enzymatically or by electrophoretic methods.

EXAMPLE 15

TREATMENT OF A DISEASE STATE IN A HUMAN PATIENT

The oligonucleotides of the invention may be used for treatment of various disease states. Treatment of a patient diagnosed with a particular disease state comprises administration of an effective dose of the oligonucleotide, in a pharmaceutically accepted formulation, to the patient via an appropriate route. The effective oligonucleotide dose depends on the disease state being treated, the severity of the disease state and the age of the patient being treated. The effective dose of an oligonucleotide may be determined based on its $IC_{50}$ and is a routine procedure for one of skill in the art. Alternatively, the effective dose of the oligomer may be determined by using the pharmacokinetics software program TopFit. For example, dosage of oligonucleotides may vary from 0.01 μg (for children) to 100 g (for adults) per kg of body weight depending on progression of the disease state. Similarly, the frequency of dosing depends on the progression of the disease state and may vary from once or more daily to once every several years.

The route of oligonucleotide administration depends on the disease state being treated. For example, administration of an oligonucleotide to a patient being treated for an inflammatory disorder may be accomplished either via oral or rectal routes. For treatment of a patient afflicted with AIDS, the most effective method of oligonucleotide administration may be an oral route or by subcutaneous injection. Cancers such as breast cancer may be treated via subcutaneous injection, while colon cancer may be treated via oral or rectal administration of the oligonucleotide. Diseases or disorders of the central nervous system may best be treated by intrathecal or intraventricular administration for delivery of the oligonucleotide to the spinal column or the brain of the patient.

Following oligonucleotide administration, the patient may be monitored for alleviation of symptoms associated with the disease state. Subsequently, the dosage may be adjusted (increased or decreased) depending upon the severity and amenability of the disease state to treatment.

It may be preferable to administer oligonucleotides of the invention in combination with other traditional therapeutics. The oligonucleotides may be administered in combination with drugs including, but not limited to, AZT for the treatment of patients afflicted with AIDS, sulfasalazine for the treatment of an inflammatory disorder such as ulcerative colitis, and 5-fluorouracil for the treatment of colon cancer.

Also, it may be desirable to administer maintenance therapy to a patient who has been successfully treated for a disease state. The dosage and frequency of oligonucleotide administration as part of a maintenance regimen may vary from 0.01 μg to 100 g per kg of body weight, ranging from once or more daily to once every 20 years.

EXAMPLE 16

INTRAVENTRICULAR ADMINISTRATION OF OLIGONUCLEOTIDES

Intraventricular drug administration, for the direct delivery of drug to the brain of a patient, may be desired for the treatment of patients with diseases afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region [*Cancer Research*, 44:1698 (1984)]. The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 μg to 100 g per kg of body weight, the pump reservoir may be refilled at 3–10 week intervals. Refilling of the pump is accomplished by percutaneous puncture of the self-sealing septum of the pump.

EXAMPLE 17

INTRATHECAL ADMINISTRATION OF OLIGONUCLEOTIDES

Intrathecal drug administration for the introduction of drug into the spinal column of a patient may be desired for the treatment of patients with diseases of the central nervous system. To effect this route of oligonucleotide administration, a silicon catheter is surgically implanted into the L3–4 lumbar spinal interspace of a human patient, and is connected to a subcutaneous infusion pump which has been surgically implanted in the upper abdominal region [*The Annals of Pharmacotherapy*, 27:912 (1993) and *Cancer*, 41:1270 (1993]. The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 μg to 100 g per kg of body weight, the pump reservoir may be refilled at 3–10 week intervals. Refilling of the pump is accomplished by a single percutaneous puncture to the self-sealing septum of the pump.

What is claimed is:

1. An oligonucleotide represented by SEQ ID NO:1 wherein at least 75% of the nucleoside units are joined together by Sp phosphorothioate 3' to 5' linkages.

2. An oligonucleotide represented by SEQ ID NO:1 wherein at least 75% of the nucleoside units are joined together by Rp phosphorothioate 3' to 5' linkages.

3. The oligonucleotide of claim 1 wherein all of the nucleoside units are joined together by Sp phosphorothioate 3' to 5' linkages.

4. The oligonucleotide of claim 2 wherein all of the nucleoside units are joined together by Rp phosphorothioate 3' to 5' linkages.

5. An oligonucleotide represented by SEQ ID NO:1 wherein all of the nucleoside units are joined together by phosphorodithioate 3' to 5' linkages.

6. A composition containing an oligonucleotide of claim 1 and an acceptable carrier.

7. A composition containing an oligonucleotide of claim 2 and an acceptable carrier.

8. A composition containing an oligonucleotide of claim 5 and an acceptable carrier.

* * * * *